United States Patent [19]

Miyashi et al.

[11] Patent Number: 4,940,832

[45] Date of Patent: Jul. 10, 1990

[54] PROCESS FOR SEPARATING 2,6-DIMETHYLNAPHTHALENE

[75] Inventors: Tsutomu Miyashi, 15-18, Hitokita 3-chome, Taihaku-ku, Sendai-shi, Miyagi; Yoshiro Yamashita, Aichi; Takanori Suzuki, Miyagi; Hiroshi Fujii, Kanagawa, all of Japan

[73] Assignees: Tsutomu Miyashi, Miyagi; Mitsubishi Oil Co., Ltd., Tokyo, both of Japan

[21] Appl. No.: 365,635

[22] Filed: Jun. 13, 1989

[30] Foreign Application Priority Data

Jun. 13, 1988 [JP] Japan ................ 63-143772

[51] Int. Cl.$^5$ ............................. C07C 7/152
[52] U.S. Cl. .................... 585/863; 585/833; 585/860
[58] Field of Search ............... 585/833, 860, 863, 865, 585/868, 864

[56] References Cited

U.S. PATENT DOCUMENTS

| 3,665,043 | 5/1972 | Davis et al. | |
|---|---|---|---|
| 3,670,039 | 6/1972 | Davis | 585/865 |
| 3,870,745 | 3/1975 | Angstadt | 585/471 |
| 3,936,509 | 2/1976 | Nagahama et al. | 585/865 |

FOREIGN PATENT DOCUMENTS

| 2449700 | 10/1974 | Fed. Rep. of Germany. |
|---|---|---|
| 47-29893 | 8/1972 | Japan. |
| 47-29894 | 8/1972 | Japan. |
| 47-29895 | 8/1972 | Japan. |
| 47-38440 | 9/1972 | Japan. |
| 47-44728 | 11/1972 | Japan. |
| 55-44734 | 11/1980 | Japan. |
| 55-47021 | 11/1980 | Japan. |
| 60-41622 | 3/1985 | Japan. |

OTHER PUBLICATIONS

European Search Report.
Chemical Abstracts, No. 18, vol. 109, Oct. 31, 1988.
Chemical Abstracts, No. 1, vol. 110, Jan. 2, 1989.
Chemical Abstracts, No. 3, vol. 110, Jan. 16, 1989.

*Primary Examiner*—Glenn Caldarola
*Assistant Examiner*—William C. Diemler
*Attorney, Agent, or Firm*—Sughrue, Mion, Zinn, Macpeak & Seas

[57] ABSTRACT

A process for separating 2,6-dimethylnaphthalene from a 2,6-dimethylnaphthalene-containing mixture which comprises mixing said mixture with a complexing agent selected from the group consisting of bis(1,2,5)-thiaziazolotetracyanoquinodimethane, (1,2,5)selenadiazotetrocyanonaphthoquinodimethane, (1,2,5)thiaziazolotetracyanonaphthoquinodimethane, 2,6-dichlorotetracyanoanthraquinodimethene, and 2,6-diiodotetracyanoanthraquinodimethane to thereby form a complex, separating a solid matter containing said complex; and decomposing the solid matter containing the same to thereby separate and collect an oil rich in the 2,6-dimethylnaphthalene. According to this process, 2,6-dimethylnaphthalene can be readily separated at a high selectivity. Further the complexing agent can be readily recovered and reused as such.

7 Claims, No Drawings

PROCESS FOR SEPARATING 2,6-DIMETHYLNAPHTHALENE

FIELD OF THE INVENTION

This invention relates to a process for separating 2,6-dimethylnaphthalene from a mixture containing 2,6-dimethylnaphthalene with the use of a tetracyanoquinodimethane (which will be abbreviated as TCNQ hereinafter) derivative. Dimethylnaphthalene will be abbreviated as DMN hereinafter.

BACKGROUND OF THE INVENTION 2,6-DMN, which may be converted into naphthalene-2,6-dicarboxylic acid by oxidation, has attracted attention as an important material for the production of industrial products such as polyesters or plasticizers. 2,6-DMN is present in a petroleum fraction or a coal tar fraction in the form of a mixture with other DMN isomers. However it is difficult to economically obtain highly pure 2,6-DMN through distillation, since there are ten DMN isomers and 2,7-DMN, among all, has a boiling point close to that of 2,6-DMN. Additionally, it is known that DMN isomers form an eutectic mixture when crystallized. In particular, 2,6-DMN forms a two-component eutectic mixture together with 2,7-DMN or 2,3-DMN, which makes it difficult to recover 2,6-DMN at a high selectivity from a DMN mixture. Accordingly there have been proposed a number of methods for separating 2,6-DMN. For example, JP-B-47-29895 and JP-B-47-38440 disclose a method wherein 2,6-DMN is separated by forming a complex thereof together with m-nitrobenzoic acid, while JP B-55-44734 discloses a method wherein 2,6-DMN is separated by forming a complex thereof with p-nitrobenzoic acid. (The term "JP-B" as used herein means an "examined Japanese patent publication"). However each of these methods requires a complicated procedure in order to collect a composition mainly comprising 2,6-DMN by decomposing the formed complex with an alkali. Further JP-B-55-47021 proposes a method for separating 2,6-DMN by forming a complex thereof with nitrobenzene derivatives, but a satisfactory selectivity can not be achieved by this method.

SUMMARY OF THE INVENTION

It is an object of the present invention to provide a process for separating and collecting 2,6-DMN at a high selectivity by forming a complex thereof with a specific complexing agent followed by a simple procedure.

Accordingly the present invention provides a process for separating 2,6-DMN from a 2,6-DMN-containing mixture which comprises mixing the 2,6-DMN-containing mixture (which will be simply called a mixture hereinafter) with a complexing agent, which is a TCNQ derivative, to thereby form a complex of the complexing agent and 2,6-DMN; separating a solid matter containing the formed complex; and decomposing the solid matter containing the complex to thereby separate and collect an oil rich in the 2,6-DMN.

DETAILED DESCRIPTION OF THE INVENTION

The process of the present invention may be applied to any mixture as long as it contains 2,6-DMN and as long as the mixture is free from any component which might inhibit the formation of a 2,6-DMN complex or dissolve the complex. As a complex formation preventing component, a compound such as a nitrogen compound (e.g., acrylonitrile) and a sulfur compound contained in an oil fraction are acknowledged by experimentation. It is preferable to use a hydrocarbon oil which contains various DMN isomers originating from petroleum or coal tar, more preferably a fraction having a boiling point of about 240° C. to 280° C. which is obtained by catalytic cracking or catalytic reforming in refining petroleum. In addition, any other mixtures such as a product increased in the concentration of 2,6-DMN which is obtained by isomerizing a DMN containing mixture decreased in the concentration of 2,6-DMN after separating 2,6-DMN, a product which is obtained by methylating naphthalene or methylnaphthalene, and a product which is obtained by disproportionating methylnaphthalene and the like can be applied to the present invention. As a matter of fact, the concentration of 2,6-DMN in the separated oil would advantageously increase with an increase in the 2,6-DMN content in the starting mixture. It is preferable that the mixture contains about 1% by weight or more, preferably about 5% by weight or more, of 2,6-DMN.

Examples of the complexing agent useful in the process of the present invention are as follows:

Bis(1,2,5)thiaziazolotetracyanoquinodimethane of the following formula (I) which will be abbreviated as BTDA-TCNQ hereinafter;

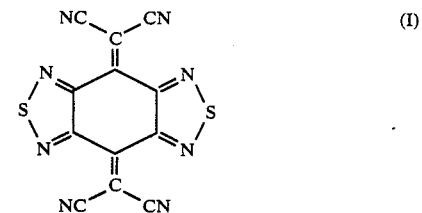

2,6-Dichlorotetracyanoanthraquinodimethane of the following formula (II) which will be abbreviated as 2,6-Cl$_2$-TCNAQ hereinafter;

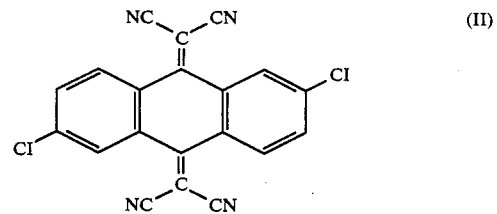

2,6-Diiodotetracyanoanthraquinodimethane of the following formula (III), which will be abbreviated as 2,6-I$_2$-TCNAQ hereinafter;

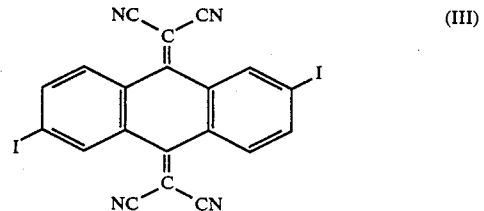

(1,2,5)Thiaziazolotetracyanonaphthoquinodimethane of the following formula (IV), which will be abbreviated as TDA-TCNNQ hereinafter;

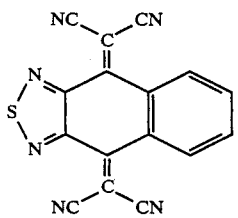

and
(1,2,5)Selenadiazolotetracyanonaphthoquinodimethane of the following formula (V), which will be abbreviated as SeDA-TCNNQ hereinafter;

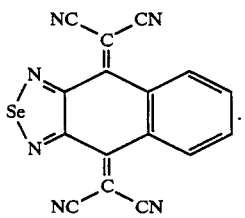

One of the these TCNQ derivatives may be selected as a complexing agent in the process of the present invention.

The complexing agent may be generally added to the mixture in such an amount as to give a ratio of the 2,6-DMN to the complexing agent of about 10/1 by mol or below. When BTDA-TCNQ is to be used as the complexing agent, the above ratio preferably ranges from about 0.5/1 to 5/1, by mol. When 2,6-Cl$_2$-TCNAQ or 2,6-I$_2$-TCNAQ is to be used, this ratio preferably ranges from about 0.5/1 to 5/1 by mol. When TDA-TCNNQ or SeDA-TCNNQ is to be used, this ratio preferably ranges from about 0.3/1 to 4/1 by mol.

The preparation method of the complexing agent to be used in the present invention is disclosed, e.g., in JP-A-62-33157 (The term "JP-A" as used herein means an "unexamined published Japanese patent application") and "The Synthesis and Properties of Tetracyanoqinodimethanes Fused with Aromatic Rings and Heterocyclic Rings" (Nippon Kagaku Kaishi, No. 3, pages 268 to 275 (1986)).

When the mixture is a liquid, it may be contacted with the complexing agent as such. Or when it is a liquid or a solid, it may be dissolved in a light hydrocarbon solvent such as petroleum ether, n-pentane, n-hexane or n-heptane, benzene, toluene or a chlorinated paraffin solvent such as dichloromethane or chloroform to thereby give a solution. To the resulting solution, the complexing agent is added in the form of a powder and the mixture obtained is stirred at about −30° C. to 220° C.

The formation of a complex may be appropriately conducted at a temperature of about −30° C. to 150° C., more preferably about 0° C. to 100° C. During this period, stirring may be continued if required. The formation of the complex requires approximately one minute to 48 hours, depending on the composition of the mixture and/or the conditions under which the complex is to be formed.

The necessary solvent amount is an amount that can dissolve the mixture.

Solid matter containing the complex thus formed may be separated by a conventional solid/liquid separation procedure such as filtration, centrifugation or precipitation. The solid matter may be washed with a light paraffinic hydrocarbon solvent such as petroleum ether, n pentane, n-hexane or n-heptane, methanol or ethanol to thereby further elevate the purity of the 2,6-DMN.

Next, an oil rich in 2,6-DMN may be collected from the solid matter containing the complex by thermal decomposition or decomposition with other compounds such as esters, ethers, acetonitrile, aromatic hydrocarbons, chlorinated paraffins, alcohols, ketones, or paraffinic hydrocarbons. Among these methods, thermal decomposition is preferable since it permits one to directly recover the separated oil and it enables the reuse of the complexing agent as such after separating the oil, and it is necessary for decomposition using other compounds to include a collecting step for the separated oil and the complexing agent. The thermal decomposition may be carried out by heating the solid matter to, in general, about 50° C. to 200° C., under reduced pressure of, in general, about 1 mmHg to 50 mmHg, to thereby enable the reuse of the complexing agent. It is preferable to conduct the thermal decomposition under a reduced pressure of about 1 mmHg to 50 mmHg at a temperature of about 130° C. to 180° C. (in the case of BTDA-TCNQ), about 100° C. to 150° C. (in the case of 2,6-Cl$_2$-TCNAQ or 2,6-I$_2$-TCNAQ), or about 140° C. to 190° C. (in the case of TDA-TCNNQ or SeDA-TCNNQ). In each case, the complexing agent may be repeatedly used after the completion of the decomposition.

It is also possible to further enhance the purity of the 2,6-DMN by repeatedly subjecting the oil thus separated to the formation of a solid matter containing the complex and the decomposition product.

Accordingly, the present invention provides an industrially advantageous process which enables not only ready separation and collection of 2,6-DMN at a high selectivity, compared with conventional methods, but also the reuse of the complexing agent.

To further illustrate the present invention, and not by way of limitation, the following examples will be given.

EXAMPLE 1

To 18.0 g of a starting oil which was a fraction of a catalytically reformed petroleum oil having a boiling point of 250° C. to 270° C. and employed as a 2,6-DMN-containing mixture, 986 mg of a powder of BTDA-TCNQ (100 to 325 mesh) was added and the resulting mixture was heated to 170° C. under stirring. Then it was allowed to cool at room temperature under stirring for four hours. The precipitate thus formed was filtered and washed with n-hexane. After drying under 5 mmHg pressure, 1.41 g of soild matter containing a complex were obtained. This solid matter was thermally decomposed at 150° C. under 14 mmHg pressure and the gas thus evolved was cooled to thereby collect 461 mg of a separated oil. The residual yellow crystals were identified as BTDA-TCNQ by elemental analysis and infrared analysis. Table 1 shows the composition of the starting oil and that of the separated oil each determined by gas chromatography.

EXAMPLE 2

448 mg of the separated oil which was collected in Example 1 was dissolved in 2.2 g of dichloromethane and 180 mg of a powder of BTDA-TCNQ (100 to 325 mesh) was added thereto. Then the resulting mixture was stirred at room temperature for two hours. The precipitate thus formed was filtered and washed with n-hexane. After drying under 5 mmHg pressure, 267 mg of solid matter containing a complex was obtained. This solid matter was thermally decomposed at 150° C. under 14 mmHg pressure and the gas thus evolved was cooled to thereby collect 87 mg of a separated oil. The residual yellow crytals were identified as BTDA-TCNQ by elemental analysis and infrared analysis. Table 1 shows the composition of the separated oil determined by gas chromatography.

EXAMPLE 3

To 3.35 g of the same starting oil as the one employed in Example 1, 181 mg of the BTDA-TCNQ recovered in Example 1 was added and the resulting mixture was heated to 170° C. under stirring. Then it was allowed to cool at room temperature under stirring for four hous. The precipitate thus formed was filtered and washed with n-hexane. After drying under 5 mmHg pressure, 258 mg of solid matter containing a complex was obtained. This solid matter was thermally decomposed at 150° C. under 14 mmHg pressure and the gas thus evolved was cooled to thereby collect 85 mg of a separated oil. The residual yellow crystals were identified as BTDA-TCNQ by elemental analysis and infrared analysis. Table 1 shows the composition of the separated oil determined by gas chromatography.

EXAMPLE 4

To 2.46 g of the same starting oil as the one employed in Example 1, 166 mg of a powder of SeDA-TCNNQ (100 to 325 mesh) was added and the resulting mixture was heated to 170° C. under stirring. Then it was allowed to cool at room temperature under stirring for 39 hours. The precipitate thus formed was filtered and washed with n-hexane. After drying under 5 mmHg pressure, 192 mg of solid matter containing a complex was obtained. This solid matter was thermally decomposed at 145° C. under 14 mmHg pressure and the gas thus evolved was cooled to thereby collect 34 mg of a separated oil. The residual grayish green crystals were identified as SeDA-TCNNQ by elemental analysis and infrared analysis. Table 1 shows the composition of the separated oil determined by gas chromatography.

EXAMPLE 5

To 3.38 g of the same starting oil as the one employed in Example 1, 199 mg of a powder of TDA-TCNNQ (100 to 325 mesh) was added and the resulting mixture was heated to 170° C. under stirring. Then it was allowed to cool at room temperature under stirring for nine hours. The precipitate thus formed was filtered and washed with n-hexane. After drying under 5 mmHg pressure, 235 mg of solid matter containing a complex was obtained. This solid matter was thermally decomposed at 145° C. under 14 mmHg pressure and the gas thus evolved was cooled to thereby collect 47 mg of a separated oil. The residual yellowish brown crystals were identified as TDA-TCNNQ by elemental analysis and infrared analysis. Table 1 shows the composition of the separated oil determined by gas chromatography.

EXAMPLE 6

To 2.00 g of the same starting oil as the one employed in Example 1, 141 mg of a powder of 2,6-$Cl_2$-TCNAQ (100 to 325 mesh) was added and the resulting mixture was heated to 170° C. under stirring. Then it was allowed to cool at room temperature under stirring for eight hours. The precipitate thus formed was filtered and washed with n-hexane. After drying under 5 mmHg pressure, 188 mg of solid matter containing a complex was obtained. This solid matter was thermally decomposed at 130° C. under 14 mmHg pressure and the gas thus evolved was cooled to thereby collect 56 mg of a separated oil. The residual orange crystals were identified as 2,6-$Cl_2$-TCNAQ by elemental analysis and infrared analysis. Table 1 shows the composition of the separated oil determined by gas chromatography.

EXAMPLE 7

To 1.50 g of the same starting oil as the one employed in Example 1, 158 mg of a powder of 2,6-$I_2$-TCNAQ (100 to 325 mesh) was added and the resulting mixture was heated to 170° C. under stirring Then it was allowed to cool at room temperature under stirring for eight hours. The precipitate thus formed was filtered and washed with n-hexane. After drying under 5 mmHg, pressure 192 mg of solid matter containing a complex was obtained. This solid matter was thermally decomposed at 140° C. under 14 mmHg pressure and the gas thus evolved was cooled to thereby collect 42 mg of a separated oil. The residual yellow crystals were identified as 2,6-$I_2$-TCNAQ by elemental analysis and infrared analysis. Table 1 shows the composition of the separated oil determined by gas chromatography.

COMPARATIVE EXAMPLE 1

To 20.0 g of the same starting oil as the one employed in Example 1, 5.0 g of m nitrobenzoic acid was added and the resulting mixture was heated to 100° C. for 15 minutes. Then it was allowed to cool and the precipitate thus formed was filtered and washed with petroleum ether. Thus solid matter containing a complex was collected. This solid matter was dissolved in ethyl ether and washed with 5% caustic soda several times and then with water. After distilling off the ether, 340 mg of a solid was obtained. Table 1 shows the composition of the solid thus obtained determined by gas chromatography.

TABLE 1

| Composition (wt. %) | Starting oil | Ex. 1 | Ex. 2 | Ex. 3 | Ex. 4 | Ex. 5 | Ex. 6 | Ex. 7 | Comp. Ex. 1 |
| --- | --- | --- | --- | --- | --- | --- | --- | --- | --- |
| Methylnaphthalene | 8.8 | 3.5 | 0.1 | 3.7 | 1.3 | 5.4 | 12.8 | 3.0 | 24.2 |
| Ethylnaphthalene | 7.9 | 1.1 | 0.0 | 0.8 | 0.0 | 1.6 | 10.8 | 4.8 | 0.4 |
| 2,6-DMN | 9.7 | 73.5 | 99.2 | 75.6 | 97.2 | 37.8 | 22.3 | 42.6 | 45.3 |
| 2,7-DMN | 9.4 | 7.0 | 0.6 | 6.4 | 1.1 | 10.5 | 9.3 | 9.1 | 5.9 |
| Other DMN isomers | 46.3 | 14.3 | 0.1 | 13.1 | 0.4 | 39.7 | 42.5 | 38.1 | 7.0 |
| Biphenyl etc. | 17.9 | 0.6 | 0.0 | 0.4 | 0.0 | 5.0 | 2.3 | 2.4 | 17.2 |

EXAMPLE 8

A solid matter (raw solid) containing the complex which is obtained by the same manner as in Example 1 using BTDA-TCNQ was mixed with each of the compounds for the complex decomposition shown in Table 2 at 20° C. for one hour under stirring. The residual solid was filtered, washed with n-hexane, and dried under 5 mmHg pressure. The amounts of BTDA-TCNQ contained in the dried raw solid and the dried residual solid were determined to obtain the decomposition rate of the complex. The results are shown in Table 2.

The decomposition rate is a value which is obtained by subtracting a ratio of (the complexing agent which forms the complex of the residual solid) to (the complexing agent which forms the complex of the raw solid) from 1 and multiplying it by 100.

TABLE 2

| Compound | Amount (g) | Raw solid (mg) | Residual solid (mg) | Complex decomposition rate (%) |
|---|---|---|---|---|
| Ethyl acetate | 72.2 | 178.2 | 57.7 | 68 |
| Acetonitrile | 63.0 | 190.8 | 78.7 | 61 |
| Toluene | 47.6 | 198.8 | 45.3 | 77 |
| Methylene chloride | 24.5 | 202.1 | 127.1 | 84 |
| Diethyl ether | 107 | 198.9 | 146.9 | 63 |
| Methanol | 119 | 200.1 | 151.5 | 29 |
| n-Hexane | 99.0 | 164.8 | 145.5 | 18 |

Accordingly, the process of the present invention for collecting an oil rich in 2,6-DMN from a mixture containing the same which comprises contacting the mixture with a complexing agent and collecting the 2,6-DMN from a solid matter containing the complex thus formed is easily operated and is excellent in selectivity for 2,6-DMN and in the separation selectivity (efficiency) of the same from the complex. Namely, a complex of 2,6-DMN with the complexing agent can be formed at a high selectivity by simply mixing the 2,6-DMN-containing mixture with the complexing agent and stirring. When the mixture is a liquid, the complex may be formed by mixing it as such with the complexing agent. When the mixture is a solid, it may be dissolved in a solvent first and then form a complex. The subsequent procedure may be conducted by, for example, a known simple solid/liquid separation method. Then the 2,6-DMN may be collected from the complex thus separated at a high purity by a simple treatment such as heating under reduced pressure. The process of the present invention is further advantageous in that, for example, the complexing agent which is regenerated simultaneously with the collection of the product may be repeatedly reused as such.

While the invention has been described in detail and with reference to specific examples thereof, it will be apparent to one skilled in the art that various changes and modifications can be made therein without departing from the spirit and scope thereof.

What is claimed is:

1. A process for separating 2,6-dimethylnaphthalene from a 2,6-dimethylnaphthalene containing mixture which comprises mixing said 2,6-dimethylnaphthalene-containing mixture with a complexing agent selected from the group consisting of compounds A to E to thereby form a complex of the complexing agent and 2,6-dimethylnaphthalene; separating a solid matter containing the complex of the complexing agent and 2,6-dimethylnaphthalene thus formed; and decomposing said solid matter containing said complex to thereby separate and collect an oil rich in the 2,6-dimethylnaphthalene:

A. Bis(1,2,5)thiaziazolotetracyanoquinodimethane:

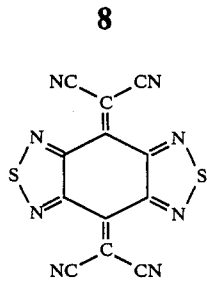

bis(1,2,5)thiazizolotetracyanoquinodimethane,

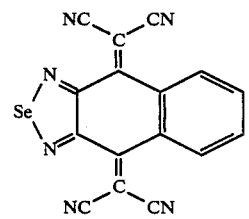

C. (1,2,5)Thiaziazolotetracyanonaphthoquinodimethane:

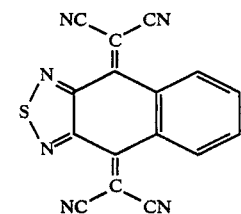

D. 2,6-Dichlorotetracyanoanthraquinodimethane:

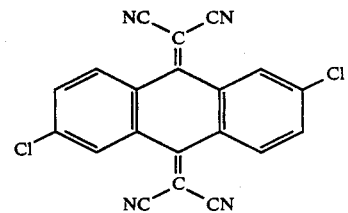

E. 2,6-Diiodotetracyanoanthraquinodimethane:

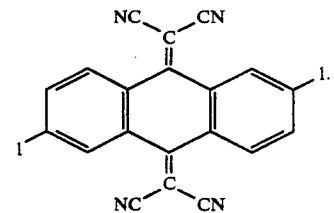

2. A process for separation 2,6-dimethylnaphthalene as set forth in claim 1, wherein said 2,6-dimethylnaphthalene containing mixture is a hydrocarbon oil.

3. A process for separating 2,6-dimethylnaphthalene as set forth in claim 1, wherein said 2,6-dimethylnaphthalene-containing mixture is a fraction having a boiling point of 240° C. to 280° C. of a catalytically reformed petroleum oil or a petroleum catalytically cracked petroleum oil.

4. A process for separating 2,6-dimethylnaphthalene as set forth in claim 1, wherein said 2,6-dimethylnaphthalene-containing mixture is dissolved in a light hydrocarbon solvent or a chlorinated paraffin solvent prior to mixing with said complexing agent.

5. A process for separating 2,6-dimethylnaphthalene as set forth in claim 1, wherein the mixing of said 2,6-dimethylnaphthalene-containing mixture with said complexing agent is carried out at a temperature of 0° to 100° C.

6. A process for separating 2,6-dimethylnaphthalene as set forth in claim 1, wherein the decomposing of said solid matter containing the complex of 2,6-dimethylnaphthalene and said complexing agent is carried out by heating said solid matter containing the complex to 50° to 200° C. under a reduced pressure of 1 mmHg to 50 mmhg.

7. A process for separating 2,6-dimethylnaphthalene as set forth in claim 1, wherein said solid matter containing the complex of 2,6-dimethylnaphthalene and said complexing agent is thermally decomposed under reduced pressure and the complexing agent thus collected is circulated and reused in a subsequent formation of the complex.

* * * * *

UNITED STATES PATENT AND TRADEMARK OFFICE
CERTIFICATE OF CORRECTION

PATENT NO. : 4,940,832

DATED : July 10, 1990

INVENTOR(S) : Tsutomu MIYASHI et al.

It is certified that error appears in the above-identified patent and that said Letters Patent is hereby corrected as shown below:

ON THE TITLE PAGE: At [73] "Assignees:" please delete "Tsutomu Miyashi, Miyagi; Mitsubishi Oil Co., Ltd., Tokyo, both of Japan" and insert --Mitsubishi Oil Co., Ltd., Tokyo, Japan--.

At [57] in the ABSTRACT, on line 6, delete "(1,2,5)-selenadiazotetro-cyanonaphthoquinodimethane" and insert --(1,2,5)-selenadiazolotetro-cyanonaphthoquinodimethane--.

IN THE CLAIMS: In claim 1, at column 8, line 11, delete "bis(1,2,5)thiazizolotetracyano-quinodimethane" and insert --B.(1,2,5)-selenadiazolotetro-cyanonaphthoquinodimethane--.

Signed and Sealed this

Twenty-first Day of January, 1992

Attest:

HARRY F. MANBECK, JR.

*Attesting Officer*  *Commissioner of Patents and Trademarks*

UNITED STATES PATENT AND TRADEMARK OFFICE
CERTIFICATE OF CORRECTION

PATENT NO. : 4,940,832
DATED : July 10, 1990
INVENTOR(S) : Tsutomu MIYASHI et al.

It is certified that error appears in the above-identified patent and that said Letters Patent is hereby corrected as shown below:

ON THE TITLE PAGE: At [57] in the ABSTRACT, on line 6, delete "selenadiazotetrocyanonaphthoquinodimethane" and insert therefor --selenadiazotetracyanonaphthoquino-dimethane--.

AT COLUMN 3: Line 48, after "light" insert --paraffinic--

AT COLUMN 4: Line 25, delete "2,6-$Cl_{12}$-" to read --2,6-$Cl_2$- --.

AT COLUMN 8: Line 11, delete "bis(1,2,5)thiazizolotetracyano-quinodimethane" to read --B. (1,2,5)Selenadiazolo-tetracyanonaphthoquinodimethane--.

AT COLUMN 10: Line 3, delete "mmhg" to read --mmHg--.

Signed and Sealed this

Fifth Day of May, 1992

Attest:

DOUGLAS B. COMER

*Attesting Officer*   *Acting Commissioner of Patents and Trademarks*